United States Patent [19]

Anderson et al.

[11] Patent Number: 4,540,280

[45] Date of Patent: Sep. 10, 1985

[54] FIBER OPTIC THIN-LAYER CELL

[75] Inventors: James L. Anderson; Jeffrey D. Brewster, both of Athens, Ga.

[73] Assignee: University of Georgia Research Foundation, Inc., Athens, Ga.

[21] Appl. No.: 445,959

[22] Filed: Dec. 1, 1982

[51] Int. Cl.$^3$ ............................................. G01N 21/01
[52] U.S. Cl. ........................................ 356/246; 356/440
[58] Field of Search .......................... 356/319, 246, 440

[56] References Cited

U.S. PATENT DOCUMENTS

| | | | |
|---|---|---|---|
| 3,740,158 | 6/1973 | Bellinger et al. | 356/246 |
| 3,941,567 | 3/1976 | Combaz | 356/246 X |
| 4,076,420 | 2/1978 | De Maeyer et al. | 356/246 X |
| 4,405,235 | 9/1983 | Rossiter | 356/246 |

FOREIGN PATENT DOCUMENTS 2231873  1/1974  Fed. Rep. of Germany ...... 356/246

Primary Examiner—Davis L. Willis
Assistant Examiner—Matthew W. Koren
Attorney, Agent, or Firm—Sumner C. Rosenberg

[57] ABSTRACT

A fiber optic thin-layer cell for use in spectrophotometric analysis of liquid or gaseous matter, and a related method of spectrophotometric analysis, which comprises the use of fiber optics in conjunction with low-volume thin-layer cells to direct a source of light into an enclosed cell area in which a sample is held for analysis, and to receive of the light after it passes through the sample and direct the light to a means of photometric detection. The individual fibers of the incoming and outgoing bundles of fiber optics are disposed generally along the plane of the cell, on opposite sides, so that the light is directed through the width of the cell area and along its length.

63 Claims, 4 Drawing Figures

FIBER OPTIC THIN-LAYER CELL

BACKGROUND OF THE INVENTION

This invention pertains to cells for holding matter to be analyzed by spectrophotoanalysis, and more particularly to such cells which only require small volumes of material to be analyzed and provide high optical sensitivity. In addition, this invention has to do with such cells as designed for use in spectroelectrochemical analysis.

Spectroelectrochemistry is widely used for the study of the mechanisms and kinetics of electrode reactions as well as the characterization of electrogenerated species. The technique is frequently employed for the study of biological redox systems, including multicomponent systems. In such applications, it is frequently essential that the consumption of precious enzymes be minimized by employing cells which feature low volume and high optical sensitivity. These characteristics are also essential for the development of spectroelectrochemical systems for analytical applications.

Several approaches to the problem of minimizing sample volume have been pursued. These include miniaturized conventional cells, circulating cells, including multispectral and circulating long optical path (CLOSET) cells, optically transparent thin-layer electrode cells (OTTLE), and multiple specular reflectance (MSR) cells. All of these approaches have disadvantages. The miniaturized conventional and CLOSET cells have volumes of hundreds of microliters with relatively small surface area/volume ratios, and the samples therein must be stirred to achieve reasonable rates of electrolysis. Stirring may in some cases lead to denaturation of some delicate proteins. OTTLE cells require less volume than conventional or CLOSET cells, but the OTTLE cell has a very low optical sensitivity compared to conventional designs, and therefore requires much higher concentrations of chromophore to obtain comparable response, partially negating the advantage of low volume. Thus, the total quantity of enzyme required for an OTTLE cell may equal the quantity required for a much larger volume CLOSET cell which has greater optical sensitivity. The MSR cell is limited by the requirement for a laser source, and precise alignment of the optical elements. The OTTLE and MSR designs also suffer from the requirement for electrodes with specific optical properties, i.e., transparent (OTTLE) or reflective (MSR) electrodes.

Techniques have also been developed for kinetic studies in which a highly collimated beam is passed at a small angle or parallel to the electrode, using both laser and conventional continuum light sources. Considerable care is required in these techniques to collimate the continuum source. While the total solution volume in these techniques is quite large, the spectrally monitored region is confined to a small volume near the electrode surface and optical beam positioning is critical.

SUMMARY OF THE INVENTION

The present invention comprises a fiber optic thin-layer spectroelectrochemical analysis method with the optical path parallel to the working electrode, which successfully combines the advantages of low volume and long optical path length. The present invention also comprises fiber optic thin-layer cells which are utilized in said method. The method and apparatus are also adaptable to being used in spectrophometric mode with the same advantages.

In summary, the method invention disclosed comprises the use of fiber optics in conjunction with suitably designed low volume thin-layer cells to direct a source of light into an enclosed cell area in which a sample gas or liquid is held for spectrophotometric analysis and for receipt of the light after it passes through the sample and directing the light to a means of photometric detection. The apparatus invention disclosed herein comprises thin-layer or planar enclosed sample holding cells and bundles of optical fibers in which the individual fibers of the bundle are disposed generally along the plane of the cell in a manner that light entering the first bundle of fibers is directed into and through the enclosed cell area and picked up by the fibers of a second bundle and exits from the bundled end of the second optical fiber bundle.

By providing, in addition, an electrode material as one of the planar surfaces of the thin-layer cell, the cell may be used in connection with spectroelectrochemical analysis methods.

The fiber optic thin-layer cell disclosed herein may be made to have a long optical path while being sufficiently thin that sufficient optical sensitivity may be attained while using sample volumes much less than other methods described above. Furthermore, the present invention overcomes other disadvantages of previously described methods since it is a simple, relatively inexpensive device and easy to utilize method, not requiring stirring of samples, laser light sources, limited choice of electrode materials and optical properties, or careful and difficult optical beam positioning.

Therefore, it is an object of this invention to provide a fiber optic thin-layer cell which allows a small sample volume to be effectively analyzed by spectrophotometric or spectroelectrochemical means.

It is a further object of the present invention to provide a relatively inexpensive method of analyzing small volume samples.

It is another object of the present invention to provide a spectroelectrochemical method for more easily analyzing small volume samples.

DESCRIPTION OF THE INVENTION

Figure 1:
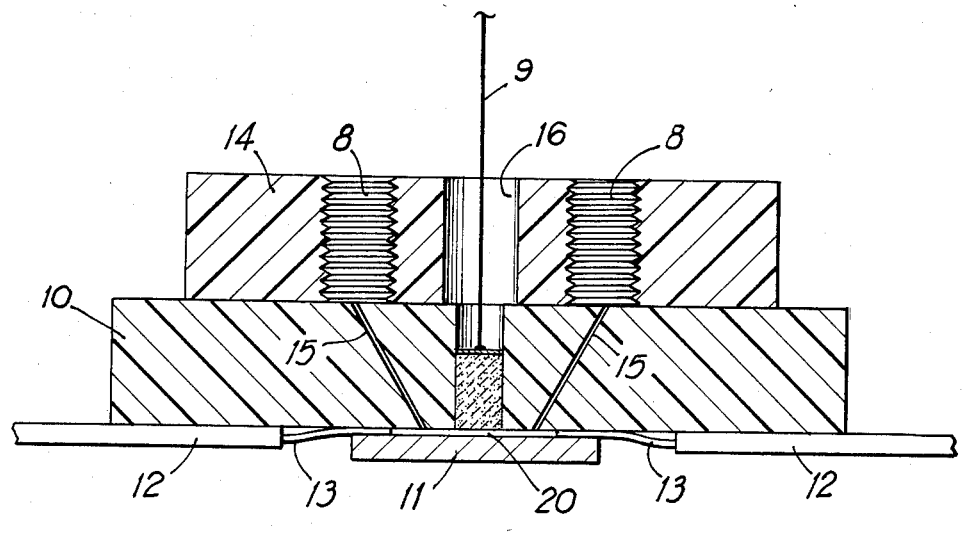
FIG. 1 is a cross-section of a complete fiber optic thin-layer cell.

FIG. 1 shows a fiber optic thin-layer cell for use in spectroelectrochemical analysis. The upper cell body, which forms one wall of the optical cell 20 is made of two pieces 10, 14 of 1 centimeter thick polymethylmethacrylate (PMMA) sheet. The upper body segment 14 has a 6.35 millimeter hole 16 in the center to form the reference/auxiliary electrode compartment. In addition, two inlet/outlet parts 8 tapped for standard ¼—28 plastic chromatography fittings are in the upper body segment 14, and those parts continue through the lower body segment 10 as 0.51 millimeter diameter holes 15 which are angled so as to intercet the bottom surface (the upper surface of the enclosed optical cell) 0.9 centimeter apart, for introducing and removing samples from the optical cell.

A 3 millimeter diameter, 1 centimeter long microporous glass plug 9, such as Vycor, is press-fitted into a hole drilled 0.08 millimeter undersize in the center of the lower cell body, after pre-heating the cell body to 100° C. in an oven. The excess porous Vycor is removed by sanding with 200 grit paper until flush with the PMMA bottom surface, and the entire bottom surface of the cell body is then smoothed with with 400 and 600 grit paper and polished with 1 micrometer diameter alumina on a lapping wheel. The two halves of the cell body are cemented together, and after drying, a 4.0 millimeter hole is drilled parallel to the reference chamber and about 1 centimeter from its center to provide a connection to the working electrode. The lower surface of the cell body is then thoroughly cleaned and dried.

A 2 millimeter wide bead of epoxy cement is applied to the lower surface of the cell body to form a 1.5 centimeter square centered on the porous Vycor frit 9.

The optical cell is constructed by sandwiching optical fibers 13 from noncoherent glass optical fiber light guide bundles 12 between the lower surface of the cell body and a 2.5 millimeter square tin oxide electrode 11. The optical fiber bundles contain 200 coated fibers of 56 micrometers diameter (core diameter 50 micrometers, core refractive index 1.62, numerical aperture 0.66), and the plastic sheathing and reinforcing fibers are removed from the ends of two fiber bundles, exposing 4 centimeters of fiber. The fiber bundles are centered on opposite sides of the 1.5 centimeter square bead of epoxy, with their ends 1.0 centimeter apart. The fibers are pushed into the cement, forming a flat array about 1 centimeter wide. The ends of the fibers are kept free of cement while the remainder of the fiber in contact with the slide is completely embedded in cement. Excess cement is pushed outward so that a bead about 0.5 millimeter thick is left around the periphery of the fiber array. The electrode 20 is then placed carefully over the beads of epoxy and slight pressure is applied to form a seal around the periphery of the cell and reduce its thickness to about 0.2 millimeter.

Figure 2:
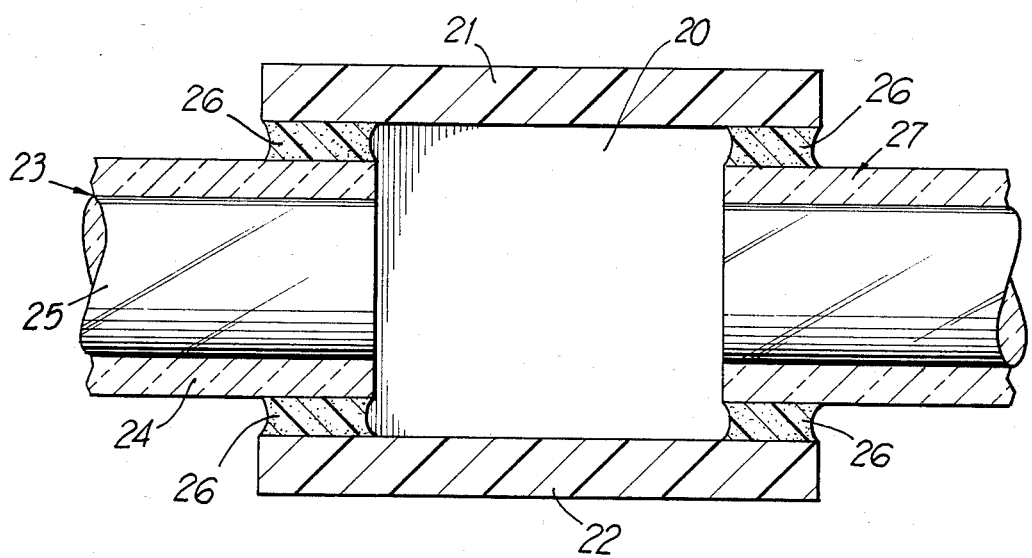
FIG. 2 is a cross-section through two exaggerated size optical fibers and the enclosed sample space of a fiber optic thin-layer cell.

FIG. 2 shows a cross-section through the cell area 20 and two optical fibers 23, 27 which exaggerates the relative size of the fibers to the thickness of the cell. Each fiber has a core 25 surrounded by a sheath 24. The fibers are sealed within the upper cell body 21 and lower cell body 22 by epoxy 26. The ends of the fibers are not covered by the epoxy and will be in contact with samples within the optical cell 20.

Figure 3:
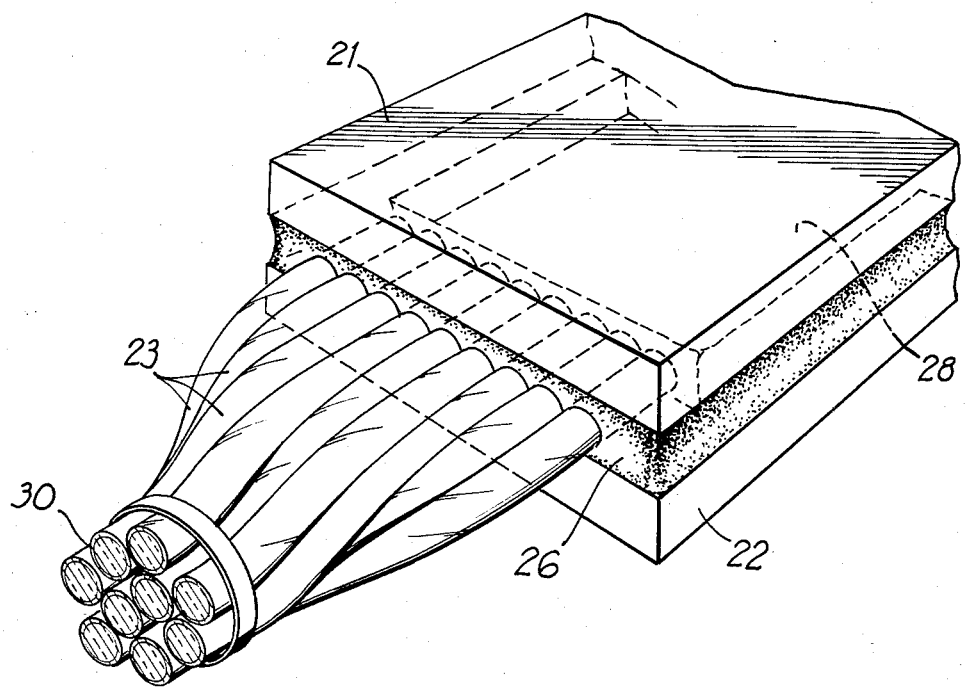
FIG. 3 is a view of a portion of a fiber optic thin-layer cell showing an array of optical fibers (size exaggerated) from one optical fiber bundle entering an edge of the cell.

FIG. 3 shows one end of a simplified optical cell where the size of individual optical fibers 23 is exaggerated for clarity. This figure shows the fibers 23 emanating from a bundle of fibers 30, and illustrates how the fibers are spread out in an array along the length of one end of the optical cell and are encased in the epoxy sealer 26 and go through the epoxy into the cell space 28. In the actual cell the fibers 23 are much smaller and much more numerous, and the gap between the upper cell wall 21 and lower cell wall 22 is much narrower. In addition, the fibers may not be strictly lined up as shown in FIG. 3, but instead may be randomly located in the space formed between the upper and lower cell walls 21, 22 at the end of the cell. But the bundles of fibers taken as a whole will direct light from one end of the planar space between the cell walls, across the enclosed cell space 28 towards a similar array of fibers at the other end of the cell.

In order to use the fiber optic thin-layer cell shown in FIG. 1, the reference/auxiliary electrode chamber is filled with 1M KCl. Both reference and auxiliary electrodes are silver wires electrolytically coated with silver chloride. A nichrome wire and a drop of mercury provides electrical contact to the working electrode. The working electrode may be any conductor or semiconductor with suitable properties, such as n-type tin oxide or platinum vapor, deposited on appropriate material, such as glass or metal. The cell resistance between working and auxiliary electrodes, measured with a high frequency bridge, is about 1000 ohms for a 1M KCl electrolyte solution for the geometry described above and will vary with specific configuration.

A spectrophotometric optical configuration may be used with the two fiber optic lightguide bundles coupling the monochromator light source to dual photomultiplier tube (PMT) detectors (EMI 9781R and/or Hamamatsu R-508-01). The interface between the monochromator and the bundles consists of a rectangular array of fibers formed by stripping 2 centimeters of sheathing from both a reference and the sample bundle and encasing them together in a section of heat-shrinkable polyolefin tubing. While still warm the tubing is compressed to a narrow rectangle with smooth-faced pliers and allowed to cool. The end of the array is cut off with a razor to expose the fiber ends and then cemented into a 9.52 millimeter outside diameter aluminum tube and secured with a set screw in an X-Y positioner mounted at the output slit of the monochromator. Positioning may be optimized by rotation of the fiber bundle interface and adjustment of the X-Y position until maximum light output is obtained simultaneously through both fiber bundles. The reference fiber bundle is connected directly between the monochromator output and the reference PMT. The sample fiber bundle is connected to the optical cell as described above. Light transmitted by the optical cell is carried to the sample PMT via the output fiber bundle, attached to the optical cell as described above. The ends of both sample and reference output fiber bundles are cemented into 7.5 centimeter long aluminum tubes of 9.52 millimeter outside diameter and 2.54 millimeter inside diameter, which were positioned by means of set screws in X-Y positioners mounted on the PMT housings. X-Y positioners may be adjusted to achieve maximum photocurrent at each PMT.

For an illustration of hook-up of the invention, the following example is given. Both the monochromator (Instruments SA model H-20) and photomultiplier tubes are mounted on a light tight box and fitted with X-Y positioners which mate with the aluminum tubes on the ends of the fiber bundles. Both a 100 W GE Quartz line lamp, and a brighter 50 W automotive quartz-halogen lamp with a more compact filament may be used as sources. Both lamps give equivalent output at the detector for the wavelengths used. A variable autotransformer is used to supply lamp power. The high voltage for the detectors is passed from a Fluke 412B power supply through a 500K ohm variable potentiometer bridge to give an independently adjustable voltage at each tube. A Philbrick model 4367 negative log-ratio amplifier and a Houston Instruments model 100 X-Y recorder may be used to display absorbence information. A battery and a 10 turn 1K ohm potentiometer coupled to the grating lead screw are used to provide a recorder input voltage proportional to wavelength. Spectra are recorded manually at a rate of approximately 10 nm/s.

The photomultiplier voltages are adjusted to give a peak photocurrent of approximately 2 $\mu$A at 520 nm. Typical voltages are 400 V and 600 V for the reference and sample tubes, respectively. For measurements in the 400 nm region, the sample photomultiplier voltage may be increased to 900 V to give a photocurrent of approximately 1 $\mu$A at 420 nm. This increase is necessary due to the sharp dropoff in the transmittance of the fibers and in source intensity at shorter wavelengths. The short-wavelength rolloff of throughput is much more marked for glass optical fibers than for conventional glass lens/air optical trains, due to a much larger optical pathlength through the absorbing medium of the fibers.

Electrochemical measurements are made with a Bioanalytical Systems CV-1B cyclic voltammetry apparatus. Potentials are recorded vs. a Ag/AgCl/1M KCl reference electrode. Potentiostatic titrations are conducted by setting the applied potential with the initial potential control of the potentiostat and holding the working electrode at that potential for 20 minutes before recording a spectrum. Theoretical transmittance calculations for the fiber optic light guide and the spectroelectrochemical cell are carried out on a microcomputer.

Figure 4:
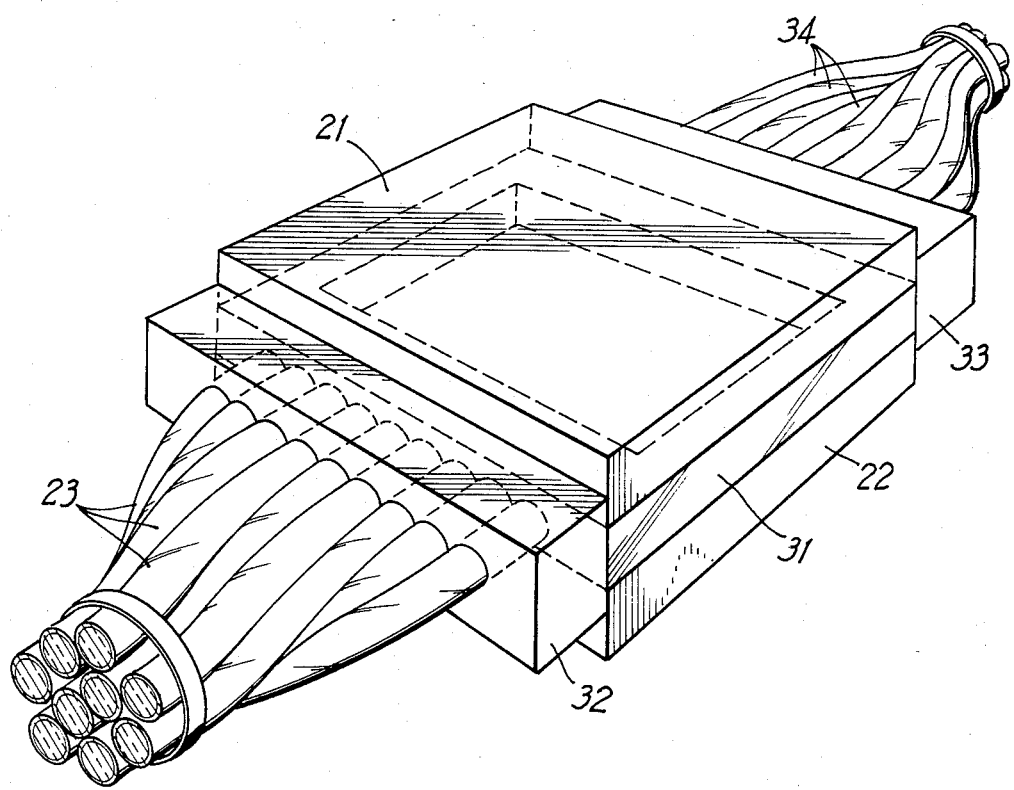
FIG. 4 is an alternative embodiment of a fiber optic thin-layer cell design.

FIG. 4 shows an alternative embodiment of the fiber optic thin-layer cell which comprises the upper cell body 21 and lower cell body 22 with a light transparent spacer 31 between them which forms a frame that defines the dimensions of the enclosed cell space. In this embodiment the optical fiber array 23, as previously described, is mounted inside a holding device 32 so that the ends of the fibers may be butted up against the spacer 31 and positioned so that the array of fibers can direct light through the spacer and along the length of the edge of the enclosed cell space. A similar holding device 33 may be positioned at the opposite side edge of the space so that the light going through the cell space and the opposite side of the spacer may be received by the optical fiber array 34 held inside the holding device 33. The spacer 31 may be made of glass, quartz, plastic or any material that transmits the wavelength of light used. The enclosed cell space may be sealed by means of matching gaskets between the spacer and the two cell body pieces. If quartz is used for the spacer and for the cell bodies, the space may be sealed by heating the optical cell to about 850° C. with pressure in a glass working oven.

Other materials which may be used for spacers or body parts include Vycor, sapphire, or diamond.

In another embodiment the optical fibers at one end of each of the two light guide bundles may be intermixed to form one combined array of fibers which separate into the two bundles. The combined array may be installed at one edge of the cell as described by either of the previously described means of joining fiber optic arrays with the cell. By providing a reflective opposite edge of the enclosed cell space, so that it is perpendicular to the optical fibers, light directed into the cell from one bundle of fibers will pass through the sample within the cell, reflect off the opposite edge, and be received by the fibers of the other bundle and directed to the appropriate light sensing device.

The fiber optic thin-layer cell gives excellent spectral response and is capable of providing an optical pathlength of 1 centimeter with a volume of less than 25 microliters. Since there is no need for a transparent or highly reflective electrode, virtually any planar electrode material may be used, although reasonably smooth electrodes will afford the best results. The cell is small enough to fit into the sample chamber of a commercial spectrophotometer, and could be interfaced by the use of lenses to direct the sample beam into the entrance bundle and collect the cell output beam from the exit bundle. In a conventional double-beam-in-time instrument, it may be necessary to attenuate the reference beam with a neutral density filter to keep the spectral recording on scale, although this procedure may decrease the signal to noise ratio somewhat.

The volume of the cell could be readily reduced to about 6 $\mu$L while retaining the present thickness and optical pathlength, by simply reducing the fiber array width to 3 millimeters, and could be further reduced to less than 1 $\mu$L with a slight sacrifice in optical sensitivity. Such a cell would be of great value as a flow-through detector, especially for applications requiring low dead volume, such as microbore liquid chromatography. The availability of such a detector would permit the separation and quantitation of mixtures of electroactive or optically absorbing analytes in a single detector cell without the dead volume associated with separate detectors.

The ability to monitor spectrally a very thin film of solution at the surface of an electrode is of great importance in mechanistic and kinetic studies. The fiber optic thin-layer cell can be used to obtain spectral data with great sensitivity at any planar or even liquid electrode.

What is claimed is:

1. A fiber optic thin-layer cell for use in spectrophotometric analysis of liquid or gaseous matter, which comprises:
    (a) a lower solid cell body piece having a flat and smooth upper surface;
    (b) an upper solid cell body piece with a flat and smooth lower surface, disposed above said lower cell body piece so that the surfaces of the two cell body pieces are approximately parallel to each other and form a relatively thin planar space between the two surfaces;
    (c) a first optical fiber light guide bundle, with the individual optical fibers at one end of said bundle unbundled and spread out in a generally flat array along the inside of one side of the planar space formed by the two cell body pieces, for directing light from a light source at the other end of said bundle into the space;
    (d) a second optical fiber light guide bundle, with the individual optical fibers at one end spread out in a generally flat array along the inside of the side of the planar space opposite the fibers of said first optical fiber bundle, for receiving the light directed into the space by said first optical fiber bundle and directing the light to a light detection device for desired analysis;
    (e) means for sealing an enclosed portion of the planar space formed by said cell body pieces and for holding the ends of the individual optical fibers of the unbundled ends of said first and second optical fiber bundles in place within the enclosed space, so that the gas or liquid to be analyzed may be contained in the cell formed thereby; and (f) means for introducing and removing the matter to be analyzed into and from the cell.

2. The fiber optic thin-layer cell as described in claim 1, wherein at least one of said cell body pieces is an electrode, to allow spectroelectrochemical analysis of the matter to be analyzed.

3. The fiber optic thin-layer cell as described in claim 2, wherein said means for introducing and removing matter from the cell comprises two holes through said cell body pieces, whose interior openings are located near opposite ends of the enclosed cell space, for drawing the matter to be analyzed into and then out of the cell.

4. The fiber optic thin-layer cell as described in claim 3, wherein the enclosed cell space has a volume of less than 25 microliters.

5. The fiber optic thin-layer cell as described in claim 4, wherein the length of the enclosed cell space between the ends of said optical fiber bundles is between 2 millimeters and 20 millimeters and the thickness of the enclosed cell space is less than 0.3 millimeter.

6. The fiber optic thin-layer cell as described in claim 1, wherein the fibers of said first and second optical fiber light guide bundles are intermixed at one end and one combined flat array of fibers is spread out along the inside of one side of the planar space formed by the two cell body pieces and wherein the opposite end of the planar space has a reflective surface perpendicular to the plane of the space and oriented to direct light emanating from the optical fibers array back towards the optical fiber array.

7. The fiber optic thin-layer cell as described in claim 6, wherein the enclosed cell space has a volume of less than 25 microliters.

8. The fiber optic thin-layer cell as described in claim 7, wherein the length of the enclosed cell space between the ends of said optical fiber bundles is between 2 millimeters and 20 millimeters and the thickness of the enclosed cell space is less than 0.3 millimeter.

9. The fiber optic thin-layer cell as described in claim 1, wherein said sealing means is a cement.

10. The fiber optic thin-layer cell as described in claim 9, wherein the enclosed cell space has a volume of less than 25 microliters.

11. The fiber optic thin-layer cell as described in claim 10, wherein the length of the enclosed cell space between the ends of said optical fiber bundles is between 2 millimeters and 20 millimeters and the thickness of the enclosed cell space is less than 0.3 millimeter.

12. The fiber optic thin-layer cell as described in claim 1, wherein said cell body pieces are glass.

13. The fiber optic thin-layer cell as described in claim 12, wherein the enclosed cell space has a volume of less than 25 microliters.

14. The fiber optic thin-layer cell as described in claim 13, wherein the length of the enclosed cell space between the ends of said optic fiber bundles is between 2 millimeters and 20 millimeters and the thickness of the enclosed cell space is less than 0.3 millimeter.

15. The fiber optic thin-layer cell as described in claim 1, wherein said cell body pieces are quartz.

16. The fiber optic thin-layer cell as described in claim 15, wherein the enclosed cell space has a volume of less than 25 microliters.

17. The fiber optic thin-layer cell as described in claim 16, wherein the length of the enclosed cell space between the ends of said optical fiber bundles is between 2 millimeters and 20 millimeters and the thickness of the enclosed cell space is less than 0.3 millimeter.

18. The fiber optic thin-layer cell as described in claim 1, wherein said cell body pieces are plastic.

19. The fiber optic thin-layer cell as described in 18, wherein the enclosed cell space has a volume of less than 25 microliters.

20. The fiber optic thin-layer cell as described in claim 19, wherein the length of the enclosed cell space between the ends of said optic fiber bundles is between 2 millimeters and 20 millimeters and the thickness of the enclosed cell space is less than 0.3 millimeter.

21. The fiber optic thin-layer cell as described in claim 1, wherein said means for introducing and removing matter from the cell comprises two holes through said cell body pieces, whose interior openings are located near opposite ends of the enclosed cell space, for drawing the matter to be analyzed into and then out of the cell.

22. The fiber optic thin-layer cell as described in claim 21, wherein the enclosed cell space has a volume of less than 25 microliters.

23. The fiber optic thin-layer cell as described in claim 22, wherein the length of the enclosed cell space between the ends of said optical fiber bundles is between 2 millimeters and 20 millimeters and the thickness of the enclosed cell space is less than 0.3 millimeter.

24. A fiber optic thin-layer cell, for use in spectrophotometric analysis of liquid or gaseous matter, which comprises:
(a) lower solid cell body piece having a flat and smooth upper surface;
(b) an upper solid cell body piece with a flat and smooth lower surface, disposed above said lower cell body piece so that the surfaces of the two cell body pieces are approximately parallel to each other and form a relatively thin planar space between the two surfaces;
(c) a thin light transparent frame spacer with parallel and smooth upper and lower faces and with inner and outer edges perpendicular to the faces, sealed between said upper and lower cell body pieces to form an enclosed cell space so that gas or liquid to be analyzed may be contained therein;
(d) a first optical fiber light guide bundle, with the individual optical fibers at one end of said bundle unbundled and spread in a generally flat array no thicker than the thickness of said light transparent frame spacer, with the end of each fiber having a smooth cross-section and butted up against the outside edge of said frame spacer, for directing light from a light source at the other end of said bundle, through the light transparent frame spacer, and into the enclosed cell space;
(e) a second optical fiber light guide bundle, with the individual optical fibers at one end of said bundle unbundled and spread in a generally flat array no thicker than the thickness of said light transparent frame spacer, with the end of each fiber having a smooth cross-section and butted up against the edge of said frame spacer opposite the ends of the fibers of said first optical fiber bundle, for receiving the light directed into the enclosed cell space by said first optical fiber bundle and directing the light to a light detection source for desired analysis;
(f) means for holding the ends of the fibers of said first and second optical fiber bundles in the flat arrays and in position against the edge of the frame spacer; and (g) means for introducing and removing the matter to be analyzed into and from the cell.

25. The fiber optic thin-layer cell as described in claim 24, wherein at least one of said cell body pieces is an electrode, to allow spectroelectrochemical analysis of the matter to be analyzed.

26. The fiber optic thin-layer cell as described in claim 25, wherein said means for introducing and removing matter from cell comprises two holes through said cell body pieces, whose interior openings are located near oposite ends of the enclosed cell space, for drawing the matter to be analyzed into and then out of the cell.

27. The fiber optic thin-layer cell as described in claim 25, which further comprises two thin compressible gaskets of approximately the same shape and size of the faces of said frame spacer and located between each of the faces of said fram spacer and said two cell body pieces, and a means for holding said cell body pieces, said spacer, and said gaskets in position and compressed against each other, such that the enclosed cell space formed thereby is sealed.

28. The fiber optic thin-layer cell as described in claim 25, wherein the enclosed cell space has a volume of less than 25 microliters.

29. The fiber optic thin-layer cell as described in claim 28, wherein the length of the enclosed cell space between the ends of said optical fiber bundles is between 2 millimeters and 20 millimeters and the thickness of the enclosed cell space is less than 0.3 millimeter.

30. The fiber optic thin-layer cell as described in claim 24, wherein the fibers of said first and second optical fiber light guide bundles are intermixed at one end and one combined generally flat array of fibers is spread out and butted up against one edge of said frame spacer and an opposite edge of said spacer is reflective and oriented to direct light emanating from the optical fiber array back towards the optical fiber array.

31. The fiber optic thin-layer cell as described in claim 30, wherein the enclosed cell space has a volume of less than 25 microliters.

32. The fiber optic thin-layer cell as described in claim 31, wherein the length of the enclosed cell space between the ends of said optical fiber bundles is between 2 millimeters and 20 millimeters and the thickness of the enclosed cell space is less than 0.3 millimeter.

33. The fiber optic thin-layer cell as described in claim 24, wherein said cell body pieces are glass.

34. The fiber optic thin-layer cell as described in claim 33, wherein the enclosed cell space has a volume of less than 25 microliters.

35. The fiber optic thin-layer cell as described in claim 34, wherein the length of the enclosed cell space between the ends of said optical fiber bundles is between 2 millimeters and 20 millimeters and the thickness of the enclosed cell space is less than 0.3 millimeter.

36. The fiber optic thin-layer cell as described in claim 24, wherein said cell body pieces are quartz.

37. The fiber optic thin-layer cel as described in claim 36, wherein said spacer frame is quartz and the spacer is sealed between said two cell body pieces by heating the fiber optic thin-layer cell to approximately 850° C. under pressure.

38. The fiber optic thin-layer cell as described in claim 36, wherein the enclosed cell space has a volume of less than 25 microliters.

39. The fiber optic thin-layer cell as described in claim 38, wherein the length of the enclosed cell space between the ends of said optical fiber bundles is between 2 millimeters and 20 millimeters and the thickness of the enclosed cell space is less than 0.3 millimeter.

40. The fiber optic thin-layer cell as described in claim 24, wherein said cell body pieces are plastic.

41. The fiber optic thin-layer cell as described in claim 40, wherein the enclosed cell space has a volume of less than 25 microliters.

42. The fiber optic thin-layer cell as described in claim 41, wherein the length of the enclosed cell space between the ends of said optical fiber bundles is between 2 millimeters and 20 millimeters and the thickness of the enclosed cell space is less than 0.3 millimeter.

43. The fiber optic thin-layer cell as described in claim 24, wherein said means for introducing and removing matter from the cell comprises two holes through said cell body pieces, whose interior openings are located near opposite ends of the enclosed cell space, for drawing the matter to be analyzed into and then out of the cell.

44. The fiber optic thin-layer cell as described in claim 43, wherein the enclosed cell space has a volume of less than 25 microliters.

45. The fiber optic thin-layer cell as described in claim 44, wherein the length of the enclosed cell space between the ends of said optical fiber bundles is between 2 millimeters and 20 millimeters and the thickness of the enclosed cell space is less than 0.3 millimeter.

46. The fiber optic thin-layer cell as described in claim 24, wherein said spacer is a material selected from the group consisting of glass, quartz, plastic, Vycor, sapphire and diamond.

47. The fiber optic thin-layer cell as described in claim 46, wherein the enclosed cell space has a volume of less than 25 microliters.

48. The fiber optic thin-layer cell as described in claim 47, wherein the length of the enclosed cell space between the ends of said optical fiber bundles is between 2 millimeters and 20 millimeters and the thickness of the enclosed cell space is less than 0.3 millimeter.

49. The fiber optic thin-layer cell as described in claim 24, which further comprises two thin compressible gaskets of approximately the same shape and size of the faces of said frame spacer and located between each of the faces of said frame spacer and said two cell body pieces, and a means for holding said cell body pieces, said spacer, and said gaskets in position and compressed against each other, such that the enclosed cell space formed thereby is sealed.

50. The fiber optic thin-layer cell as described in claim 49, wherein the enclosed cell space has a volume of less than 25 microliters.

51. The fiber optic thin-layer cell as described in claim 50, wherein the length of the enclosed cell space between the ends of said optical fiber bundles is between 2 millimeters and 20 millimeters and the thickness of the enclosed cell space is less than 0.3 millimeter.

52. The fiber optic thin-layer cell as described in claim 24, wherein the enclosed cell space has a volume of less than 25 microliters.

53. The fiber optic thin-layer cell as described in claim 52, wherein the length of the enclosed cell space between the ends of said optical fiber bundles is between 2 millimeters and 20 millimeters and the thickness of the enclosed cell space is less than 0.3 millimeter.

54. A method of spectrophotometrically analyzing liquid or gaseous matter, which comprises the steps of:
(a) introducing the matter to be analyzed into a thin planar enclosed cell;
(b) directing light from a source into the cell generally parallel to the plane of the thin cell by sending the source of light into one end of a bundle of optical fibers, and forming the other end of the bundle into a flat array of spread out optical fibers, and directing the light from the array into the thin cell with the plane of the array being the same plane as the thin cell;
(c) directing the light which passes through the cell and the matter to be analyzed into another flat array of optical fibers which form an optical fiber bundle; and
(d) directing the light emanating from the other end of the bundled fibers to a light detection device for analysis of the light.

55. The method as described in claim 54, wherein the two arrays of optical fibers are incorporated into the cell such that the ends of the fibers are within the enclosed thin planar cell.

56. The method as described in claim 55, wherein the volume of the enclosed cell is less than 25 microliters.

57. The method as described in claim 55, wherein at least one surface of the thin planar enclosed cell is an electrode for spectroelectrochemical analysis, and the step of directing light into the cell comprises directing the light parallel to the surface of the electrode, and which also comprises the step of applying an electric potential to said electrode while the light is directed through the sample to be analyzed in the cell.

58. The method as described in claim 57, wherein the volume of the enclosed cell is less than 25 microliters.

59. The method as described in claim 54, wherein the walls at the opposite edges of the thin planar enclosed cell are light transparent and the steps of directing light to and receiving light from the cell comprise placing the ends of the arrays of optical fibers in light conducting relationship with the outside of such opposite edges.

60. The method as described in claim 59, wherein the volume of the enclosed cell is less than 25 microliters.

61. The method as described in claim 59, wherein at least one surface of the thin planar enclosed cell is an electrode for spectroelectrochemical analysis, and the step of directing light into the cell comprises directing the light parallel to the surface of the electrode, and which also comprises the step of applying an electric potential to said electrode while the light is directed through the sample to be analyzed in the cell.

62. The method as described in claim 61, wherein the volume of the enclosed cell is less than 25 microliters.

63. The method as described in claim 54, wherein the volume of the enclosed cell is less than 25 microliters.

* * * * *